United States Patent [19]

Klose et al.

[11] Patent Number: 4,585,771
[45] Date of Patent: Apr. 29, 1986

[54] ANTIINFLAMMATORY IMIDAZOLE DERIVATIVES

[75] Inventors: Walter Klose, Berlin, Fed. Rep. of Germany; Irmgard Boettcher, Basel, Switzerland

[73] Assignee: Schering Aktiengesellschaft, Berlin and Bergkamen, Fed. Rep. of Germany

[21] Appl. No.: 641,641

[22] Filed: Aug. 17, 1984

Related U.S. Application Data

[62] Division of Ser. No. 434,036, Oct. 13, 1982, Pat. No. 4,466,976.

[30] Foreign Application Priority Data

Oct. 13, 1981 [DE] Fed. Rep. of Germany ....... 3141063

[51] Int. Cl.<sup>4</sup> ..................... A61K 31/55; C07D 487/14
[52] U.S. Cl. ................................ 514/220; 260/245.6; 514/250; 514/393; 514/397; 544/346; 548/336
[58] Field of Search ..................... 544/346; 260/245.6; 548/336; 514/397, 211, 220, 222, 250, 393

[56] References Cited

U.S. PATENT DOCUMENTS 3,707,475 12/1972 Lombardino .................... 548/336 X
4,402,960 9/1983 Niedballa et al. .............. 548/336 X Primary Examiner—Richard A. Schwartz
Attorney, Agent, or Firm—Millen & White

[57] ABSTRACT

Imidazole derivatives of Formula I

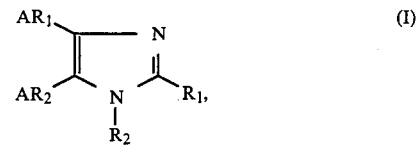

wherein $AR_1$ and $AR_2$ each independently represent phenyl optionally substituted by halogen atoms, alkyl groups, or alkoxy groups, $R_1$ is pyrrolyl, indolyl, imidazolyl, or thiazolyl, all of which are optionally substituted by lower alkyl, free or esterified carboxy or carboxyalkyl groups, benzyl, or benezenesulfonyl; and $R_2$ is hydrogen, lower alkyl, haloalkyl, or a methylene, dimethylene, trimethylene, or tetramethylene group linked to the nitrogen atom of $R_1$, and the physiologically acceptable salts thereof with acids, and when $R_1$ is substituted by carboxy, also the physiologically acceptable salts thereof with bases, are pharmacologically effective compounds, e.g., as antiinflammatories.

16 Claims, No Drawings

ANTIINFLAMMATORY IMIDAZOLE DERIVATIVES

This is a division of application Ser. No. 434,036, filed Oct. 13, 1982, now U.S. Pat. No. 4,466,976.

The present invention relates to novel imidazole derivatives, to a process for their production, and to pharmaceutical preparations containing them as active ingredients.

SUMMARY OF THE INVENTION

It is an object of this invention to provide new pharmacologically active compounds.

Upon further study of the specification and appended claims, further objects and advantages of this invention will become apparent to those skilled in the art.

These objects have been attained by providing compounds of Formula (I)

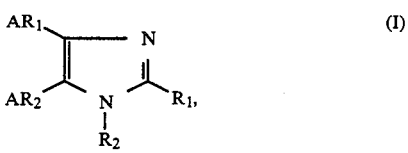

wherein
$AR_1$ and $AR_2$ each independently represent phenyl optionally substituted by halogen atoms, alkyl groups, or alkoxy groups,
$R_1$ is pyrrolyl, indolyl, imidazolyl, or thiazolyl, all of which are optionally substituted by lower alkyl, free or esterified carboxy or carboxyalkyl groups, benzyl, or benzenesulfonyl; and $R_2$ is hydrogen, lower alkyl, haloalkyl, or a methylene, dimethylene, trimethylene, or tetramethylene group linked to the nitrogen atom of $R_1$,
and the physiologically acceptable salts thereof with acids, and when $R_1$ is substituted by carboxy, also the physiologically acceptable salts thereof with bases.

DETAILED DISCUSSION

According to this invention, the substituents $AR_1$ and $AR_2$ of the imidazole derivatives are each independently phenyl optionally substituted by halogen atoms (F,Cl,Br), alkyl residues, or alkoxy residues. Usually, $AR_1$ and $AR_2$ are the same, but this is not necessary. Suitable phenyl residues $AR_1$ and $AR_2$ substituted by halogen atoms include, for example, mono- or difluorophenyl or mono- or dichlorophenyl and, in particular, p-fluorophenyl or p-chlorophenyl. Alkyl-substituted phenyl includes preferably those wherein the alkyl groups contain 1–4 carbon atoms (e.g., methyl, ethyl, propyl, isopropyl, and the like). Phenyl residues substituted by alkoxy groups include preferably those wherein the alkoxy groups contain 1–4 carbon atoms (methoxy, ethoxy, propoxy, isopropoxy, etc.).

The phenyl residues $AR_1$ and $AR_2$ can be mono- or polysubstituted with identical or different substituents. They are preferably monosubstituted, preferably in the 4-position. Especially preferred are the substituents wherein $AR_1$ and $AR_2$ each is phenyl or phenyl substituted in the para-position by fluorine, chlorine or an alkoxy group of 1–4 carbon atoms or wherein $AR_1$ and $AR_2$ each is phenyl, 4-fluorophenyl, 4-chlorophenyl, or 4-methoxyphenyl; in particular both or at least one is p-methoxyphenyl.

Preferably, the point of attachment of the $R_1$ heterocycle is a C-atom, e.g., 2-pyrrolyl, 3-pyrrolyl, 2-indole, 3-indole, 2-imidazolyl, 4- or 5-imidazolyl, or 2, 4- or 5-thiazole. The point of attachment of the substituent(s) on the heterocycle can be a C- or N-atom. Lower alkyl groups suitable as substituents include those of 1–6 carbon atoms. The carboxy-containing substituents can be esterified (COOR) by R groups which are $C_{1-6}$-alkyl.

The carboxyalkyl groups can have alkyl portions of 1–4 C atoms. The $R_1$ heterocycle can be mono- or polysubstituted.

Especially preferred residues $R_1$ are 2-pyrrolyl, 3-pyrrolyl, 7-[2,3-dihydro-1H-pyrrolizidyl], 2-indolyl, 2-imidazolyl, or 2-thiazolyl, or one of the foregoing substituted by methyl groups or lower alkoxycarbonyl groups.

The substituent $R_2$ of the imidazole derivatives of this invention can be hydrogen or alkyl of 1–6 carbon atoms, optionally substituted by halogen (F,Cl,Br,I) (preferably by bromine or iodine), or a methylene, dimethylene group, trimethylene group, or tetramethylene group linked to the nitrogen atom of $R_1$. The latter four embodiments produce pyrrolizine, pyrrolopyrazine, pyrrolodiazepin and pyrrolodiazocin rings fused to the imidazole ring in various orientations. Preferred halosubstitued alkyl residues are 2-haloethyl, 3-halopropyl, and 3-halobutyl. These compounds are preferably used as intermediates for the preparation of other compounds of this invention.

Physiologically acceptable salts of the imidazole derivatives of Formula I include, for example, salts of hydrogen chloride, hydrogen bromide, or hydrogen iodide, of sulfuric acid, phosphoric acid, and the like or salts of organic acids, such as formic acid, acetic acid, succinic acid, maleic acid, tartaric acid, or citric acid, etc.

If the imidazole derivatives of Formula I contain carboxy groups, they can form salts for example with alkali metals, such as sodium or potassium, etc.

The novel imidazole derivatives of this invention can be prepared by conventional methods. Suitable manufacturing methods include, for example, a process comprising condensing a diketone of Formula II

wherein $AR_1$ and $AR_2$ are as defined above, in the presence of ammonium ions, with an aldehyde of Formula III

wherein $R_1$ is as defined above, and the thus-obtained compounds are optionally conventionally N-alkylated and/or converted into the salts thereof.

This synthesis can be conducted under conditions known per se. (See, e.g., Arnold Weissberger: The Chemistry of Heterocyclic Compounds, Vol. 6: Klaus Hoffmann: Imidazole and Its Derivatives, Part I—Interscience Publishers Inc., New York [1953], pages 34 et seq., which is incorporated by reference herein).

The starting compounds used in this process are all known or can be readily prepared in a manner known per se. (See, e.g., Chem. Ber. 113: 2694 [1980]; Canad. J. Chem. 56: 654 [1978]; or J. Chem. Soc. 84: 635 [1962], whose disclosures are incorporated by reference herein).

The imidazole derivatives of this invention are distinguished by a pronounced antiinflammatory and antiallergic activity. Moreover, these imidazole derivatives are distinguished by a very favorable dissociation between desired pharmacological efficaciousness and undesirable—especially ulcerogenic—side effects.

The antiinflammatory activity of the compounds of this invention can be determined with the aid of conventional protocols such as the adjuvant arthritis test which is conducted as follows:

Female and male rats of the Lewis strain (LEW) with a weight span of 110-190 g are utilized. The animals receive drinking water and "Altromin" pressed feed ad libitum.

Ten rats are used for each dosage group.

*Mycobacterium butyricum* from Difko, Detroit, is utilized as the irritant. The rats were injected in the right hind paw, subplantar, with a suspension of 0.5 mg of *Mycobacterium butyricum* in 0.1 ml of thinly fluid paraffin (DAB [German Pharmacopoeia]7).

The test compounds are orally administered daily, starting with the eleventh day of the trial, over a 4 day period. The compounds are given as a clear, aqueous solution or a crystalline suspension with the addition of "Myrj" 53 (85 mg %) in an isotonic sodium chloride solution.

Experimental Design:

The rats are subdivided into groups with maximum uniformity regarding body weight. After measuring the volume of the right hind paw by plethysmography, 0.1 ml of adjuvant is injected into this paw in a subplantar fashion.

The right hind paws are measured from the 14th day of the trial to the end of the test. The duration of the trial is three weeks.

The dosage is determined at which a 40% decrease in paw volume is obtained as compared with the untreated animal ($ED_{40}$ in mg/kg body weight).

The table below shows the results obtained in this test for the compounds of this invention, compared with the previously known, structurally analogous compound 1 (see DOS No. 2,155,558).

| No. | Compound | Adjuvant Arthritis Test Dose in mg/kg Animal | % Inhibition |
|---|---|---|---|
| 1 | 4,5-Bis(4-methoxyphenyl)-2-(2-thienyl)imidazole | 4 × 10 | 12 |
| 2 | 4,5-Bis(4-methoxyphenyl)-2-(2-pyrrolyl)imidazole | 4 × 10 | 39 |
| 3 | 4,5-Bis(4-methoxyphenyl)-2-(4-methoxy-carbonyl-2-pyrrolyl)imidazole | 4 × 10 | 30 |
| 4 | 4,5-Bis(4-fluorophenyl)-2-(2-pyrrolyl)-1-(3-bromopropyl)imidazole | 4 × 10 | 21 |
| 5 | 7-[4,5-Bis(4-methoxyphenyl)-2-imidazolyl]-2,3-dihydro-1H—pyrrolizine | 4 × 10 | 31 |
| 6 | 2,3-Bis(4-methoxyphenyl)-5,6-dihydro-imidazo-[1,2-a]pyrrolo[2,1-c]pyrazine | 4 × 10 | 25 |
| 7 | 2,3-Bis(4-methoxyphenyl)-6,7-dihydro-5H—imidazo[1,2-a]pyrrolo-1,4-diazepine | 4 × 10 | 34 |
| 8 | 2,3-Bis(4-methoxyphenyl)-5,6,7,8-tetrahydro-imidazo[1,2-a]pyrrolo-[2,1-c]-1,4-diazocine | 4 × 10 | 20 |

Consequently, the novel compounds, in combination with the excipients customary in galenic pharmacy, are suitable, for example, for the treatment of acute or chronic polyarthritis, neurodermitis, bronchial asthma, hay fever, and other diseases, in mammals including humans.

It is furthermore noteworthy that the imidazole derivatives of this invention are also suitable for the treatment of migraine and dysmenorrhea.

The medical specialties of this invention can be prepared as usual, by converting the active compounds together with suitable additives, excipients, and flavoring agents into the desired forms of administration, such as tablets, dragees, capsules, solutions, inhalants, etc.

Especially suitable for oral administration are tablets, dragees, and capsules, containing, for example, 1-250 mg of active ingredient and 50 mg to 2 g of a pharmacologically inert carrier, such as, for example, lactose, amylose, talc, gelatin, magnesium stearate, and similar agents, as well as the customary additives. Typically, dosages are 10-500 mg/kg/day. Precise dosages can be readily determined by conventional considerations, e.g., in conjunction with differential potency tests based on known agents using conventional protocols. The administration of the compounds of this invention is analogous, e.g., to that of the known anti-inflammatory effective agent indometacine.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

A mixture of 18.7 g of 4,4'-dimethoxybenzil, 10.0 g of 2-formylpyrrole, 50.0 g of ammonium acetate, and 200 ml of acetic acid are placed, in a flask, into an oil bath preheated to 170° C. and stirred for 15 minutes. Then, under heating, such an amount of water is added that a permanent precipitate is produced, and this mixture is then allowed to stand overnight. The thus-obtained precipitate is filtered off and separated by chromatography on silica gel, eluent hexane/ethyl acetate (1:1). Yield: 11.2 g of 4,5-bis(4-methoxyphenyl)-2-(2-pyrrolyl)imidazole, mp 237° C.

$C_{21}H_{19}N_3O_2$ (345.407): Calculated: C 73.02 H 5.54 N 12.17. Found: C 72.90 H 5.50 N 11.87.

EXAMPLE 2

The production of 4,5-bis(4-chlorophenyl)-2-(2-pyrrolyl)imidazole takes place analogously to Example 1 by reacting 4,4'-dichlorobenzil with 2-formylpyrrole. Melting point 315° C.

$C_{19}H_{13}Cl_2N_3$ (354.251): Calculated: C 64.42 H 3.70 N 11.86 Cl 20.02. Found: C 64.58 H 3.71 N 11.42 Cl 20.31.

EXAMPLE 3

4,5-Bis(4-fluorophenyl)-2-(2-pyrrolyl)imidazole is prepared analogously to Example 1 by reacting 4,4'-difluorobenzil with 2-formylpyrrole. Melting point 276° C.

$C_{19}H_{13}F_2N_3$ (321.33): Calculated: C 71.02 H 4.08 N 13.08 F 11.82. Found: C 70.79 H 4.12 N 12.93 F 11.45.

EXAMPLE 4

4,5-Bis(4-methoxyphenyl)-2-(1-methyl-2-pyrrolyl)imidazole is produced according to Example 1 by reacting 4,4'-dimethoxybenzil with 1-methyl-2-formylpyrrole. Melting point 110° C.

$C_{22}H_{21}N_3O_2$ (359.4): Calculated: C 73.52 H 5.89 N 11.69. Found: C 73.24 H 6.05 N 11.36.

EXAMPLE 5

The preparation of 4,5-bis(4-methoxyphenyl)-2-(3-ethoxycarbonyl-2-pyrrolyl)imidazole takes place analogously to Example 1 by reacting 4,4'-dimethoxybenzil with 2-formyl-3-ethoxycarbonylpyrrole. Melting point 193° C.

$C_{24}H_{23}N_3O_4$ (417.5): Calculated: C 69.02 H 5.55 N 10.05. Found: C 68.86 H 5.98 N 10.16.

EXAMPLE 6

The production of 4,5-bis(4-methoxyphenyl)-2-(4-methoxycarbonyl-2-pyrrolyl)imidazole is conducted in analogy to Example 1 by reacting 4,4'-dimethoxybenzil with 2-formyl-4-methoxycarbonylpyrrole. Melting point 236° C.

$C_{23}H_{21}N_3O_4$ (403.4): Calculated: C 68.47 H 5.25 N 10.42. Found: C 68.51 H 5.18 N 10.12.

Preparation of starting material 3.6 g (27 millimoles) of 2-cyanopyrrole-4-carboxylic acid methyl ester, 17 g of Raney nickel, and 450 ml of 75% formic acid are introduced, in a flask, into an oil bath preheated to 120° C. and made to react for one hour. Subsequently, the mixture is poured into 1 liter of ice water and repeatedly extracted with ether. After drying and concentration of the ether phase, 1.4 g (36% of theory) of 2-formylpyrrole-4-carboxylic acid methyl ester is obtained, mp 126° C.

EXAMPLE 7

4,5-Bis(4-methoxyphenyl)-2-(1-benzyl-2-pyrrolyl)imidazole is produced analogously to Example 1 by reacting 4,4'-dimethoxybenzil with 1-benzyl-2-formylpyrrole. Melting point 183° C.

$C_{28}H_{25}N_3O_2$ (435.5): Calculated: C 77.21 H 5.78 N 9.64. Found: C 77.03 H 5.93 N 9.01.

EXAMPLE 8

The preparation of 4,5-bis(4-methoxyphenyl)-2-(1-phenylsulfonyl-2-pyrrolyl)imidazole takes place analogously to Example 1 by reacting 4,4'-dimethoxybenzil with 1-phenylsulfonyl-2-formylpyrrole. Melting point 135° C.

$C_{27}H_{23}N_3O_4S$ (485.6): Calculated: C 66.79 H 4.77 N 8.65 S 6.60. Found: C 66.81 H 4.45 N 8.52 S 6.43.

EXAMPLE 9

The production of 4,5-bis(4-methoxyphenyl)-2-(3-pyrrolyl)imidazole is conducted analogously to Example 1 by reacting 4,4'-dimethoxybenzil with 3-formylpyrrole. Melting point 232° C.

$C_{21}H_{19}N_3O_2$ (345.4): Calculated: C 73.02 H 5.54 N 12.17. Found: C 73.44 H 5.56 N 11.84.

EXAMPLE 10

4,5-Bis(4-methoxyphenyl)-2-(2-ethoxycarbonyl-3-pyrrolyl)imidazole is prepared analogously to Example 1 by reacting 4,4'-dimethoxybenzil with 2-ethoxycarbonyl-3-formylpyrrole. Melting point 176° C.

$C_{24}H_{23}N_3O_4$ (417.4): Calculated: C 69.05 H 5.55 N 10.07. Found: C 69.26 H 5.45 N 9.85.

EXAMPLE 11

2-Ethoxycarbonyl-4-[4,5-bis(4-methoxyphenyl)-2-imidazolyl]-5-methylpyrrole-3-acetic acid ethyl ester is prepared in analogy to Example 1 by reacting 4,4'-dimethoxybenzil with 2-ethoxycarbonyl-4-formyl-5-methyl-3-pyrroleacetic acid acid ethyl ester. Melting point 186° C.

$C_{29}H_{31}N_3O_6$ (517.6): Calculated: C 67.30 H 6.04 N 8.12. Found: C 67.06 H 6.22 N 7.96.

EXAMPLE 12

The production of 4,5-bis(4-methoxyphenyl)-2-(3,4,5-trimethyl-2-pyrrolyl)imidazole takes place as disclosed in Example 1 by reacting 4,4'-dimethoxybenzil with 3,4,5-trimethyl-2-formylpyrrole. Melting point 115° C.

$C_{24}H_{25}N_3O_2$ (387.5): Calculated: C 74.39 H 6.50 N 10.85. Found: C 74.10 H 6.34 N 10.93.

EXAMPLE 13

4,5-Bis(4-methoxyphenyl)-2-(3,4-dimethyl-2-pyrrolyl)imidazole is prepared analogously to Example 1 by reacting 4,4'-dimethoxybenzil with 3,4-dimethyl-2-formylpyrrole. Melting point 134° C.

$C_{23}H_{23}N_3O_2$ (373.5): Calculated: C 73.97 H 6.21 N 11.25. Found: C 73.78 H 6.30 N 11.02.

EXAMPLE 14

The preparation of 2-ethoxycarbonyl-4-[4,5-bis-(4-methoxyphenyl)-2-imidazolyl]-5-methylpyrrole-3-propionic acid ethyl ester is conducted in analogy to Example 1 by reacting 4,4'-dimethoxybenzil with 2-ethoxycarbonyl-4-formyl-5-methylpyrrole-3-propionic acid ethyl ester. Melting point 90° C.

$C_{30}H_{33}N_3O_6$ (531.6): Calculated: C 67.78 H 6.26 N 7.90. Found: C 67.45 H 6.46 N 7.83.

EXAMPLE 15

7-[4,5-Bis(4-methoxyphenyl)-2-imidazolyl]-2,3-dihydro-1H-pyrrolizine is produced analogously to Example 1 by reacting 4,4'-dimethoxybenzil with 7-formyl-2,3-dihydro-1H-pyrrolizine. Melting point 238° C.

$C_{24}H_{23}N_3O_2$ (385.4): Calculated: C 74.78 H 6.01 N 10.90. Found: C 74.60 H 6.11 N 10.64.

Preparation of starting material 13.21 g (0.1 mol) of 7-cyano-2,3-dihydro-1H-pyrrolizine is dissolved in 150 ml of absolute toluene and cooled to −20° C. To this solution is added dropwise 108 ml (0.13 mol) of a 1.2-molar diisobutyl aluminum hydride solution in toluene; the mixture is then warmed to room temperature, stirred for another hour, and decomposed with 300 ml of 10% aqueous citric acid solution. The product is extracted with methylene chloride, the organic phase is dried, concentrated, and the residue recrystallized from ether, thus obtaining 8.0 g (59% of theory) of 7-formyl-2,3-dihydro-1H-pyrrolizine, mp 58° C.

EXAMPLE 16

The production of 4,5-bis(4-methoxyphenyl)-2-(2-indolyl)imidazole takes place analogously to Example 1 by reacting 4,4'-dimethoxybenzil with 2-formylindole. Melting point 130° C.

$C_{25}H_{21}N_3O_2$ (395.5): Calculated: C 75.93 H 5.35 N 10.63. Found: C 75.61 H 5.50 N 10.38.

EXAMPLE 17

4,5-Bis(4-methoxyphenyl)-2-(3-indolyl)imidazole is prepared analogously to Example 1 by reacting 4,4'-dimethoxybenzil with 3-formylindole. Melting point 246° C.

$C_{25}H_{21}N_3O_2$ (395.5): Calculated: C 75.93 H 5.35 N 10.63. Found: C 75.81 H 5.70 N 10.49.

EXAMPLE 18

The preparation of 4,5-bis(4-methoxyphenyl)-2-(2-imidazolyl)imidazole takes place in analogy to Example 1 by reacting 4,4'-dimethoxybenzil with 2-formylimidazole. Melting point 178° C.

$C_{20}H_{18}N_4O_2$ (346.42): Calculated: C 69.35 H 5.24 N 16.18. Found: C 69.51 H 4.99 N 16.30.

EXAMPLE 19

The preparation of 4,5-bis(4-methoxyphenyl)-2-(1-methyl-2-imidazolyl)imidazole is carried out according to Example 1 by reacting 4,4'-dimethoxybenzil with 1-methyl-2-formylimidazole. Melting point 196° C.

$C_{21}H_{20}N_4O_2$ (360.4): Calculated: C 69.98 H 5.59 N 15.55. Found: C 69.78 H 5.58 N 15.43.

EXAMPLE 20

4,5-Bis(4-methoxyphenyl)-2-(1-benzyl-2-imidazolyl)imidazole is produced analogously to Example 1 by reacting 4,4'-dimethoxybenzil with 1-benzyl-2-formylimidazole. Melting Point 180° C.

$C_{27}H_{24}N_4O_2$ (436.4): Calculated: C 74.29 H 5.54 N 12.82. Found: C 73.92 H 5.71 N 12.63.

EXAMPLE 21

4,5-Bis(4-methoxyphenyl)-2-(2-thiazolyl)imidazole is prepared analogously to Example 1 by reacting 4,4'-dimethoxybenzil with 2-formylthiazole. Melting point 199° C.

$C_{20}H_{17}N_3O_2S$ (363.2): Calculated: C 66.08 H 4.72 N 11.57 S 8.83. Found: C 66.04 H 5.01 N 11.39 S 8.59.

EXAMPLE 22

1.61 g of 4,5-bis(4-methoxyphenyl)-2-(2-pyrrolyl)imidazole, 6.29 g of dibromoethane, and 1.5 g of ethyldiisopropylamine are dissolved in 120 ml of acetonitrile and heated to reflux for 48 hours. The reaction solution is then evaporated to dryness under vacuum. Separation of the 4,5-bis(4-methoxyphenyl)-2-(2-pyrrolyl)-1-(2-bromoethyl)imidazole by chromatography on silica gel with hexane/ethyl acetate (1:1) yields 0.5 g of this compound. Melting point 135° C.

$C_{23}H_{22}N_3O_2Br$ (452.349): Calculated: C 61.06 H 4.90 N 9.29 Br 17.68. Found: C 60.95 H 4.85 N 9.32 Br 17.40.

EXAMPLE 23

The preparation of 4,5-bis(4-fluorophenyl)-2-(2-pyrrolyl)-1-(3-bromopropyl)imidazole takes place analogously to Example 22 by reacting 4,5-bis(4-fluorophenyl)-2-(2-pyrrolyl)imidazole with 1,3-dibromopropane. Melting point 157° C.

$C_{22}H_{20}F_2N_3Br$ (442.301): Calculated: C 59.74 H 4.10 N 9.50 F 8.59 Br 18.07. Found: C 59.60 H 4.22 N 9.39 F 8.44 Br 18.01.

EXAMPLE 24

The preparation of 4,5-bis(4-methoxyphenyl)-2-(2-pyrrolyl)-1-(4-iodobutyl)imidazole is conducted analogously to Example 22 by reacting 4,5-bis(4-methoxyphenyl)-2-(2-pyrrolyl)imidazole with 1,4-diiodobutane. Melting point 85° C.

$C_{25}H_{26}N_3O_2I$ (527.407): Calculated: C 56.94 H 4.97 N 7.97 I 24.06. Found: C 57.20 H 5.03 N 7.48 I 23.74.

EXAMPLE 25

4,5-Bis(4-methoxyphenyl)-2-(2-pyrrolyl)-1-(3-bromopropyl)imidazole is prepared analogously to Example 22 by reacting 4,5-bis(4-methoxyphenyl)-2-(2-pyrrolyl)imidazole with 1,3-dibromopropane. Melting point 97° C.

$C_{24}H_{24}N_3O_2Br$ (466.4): Calculated: C 61.18 H 5.07 N 8.26 Br 15.42. Found: C 61.31 H 5.19 N 8.43 Br 15.70.

EXAMPLE 26

The production of 4,5-bis(4-methoxyphenyl)-2-(2-pyrrolyl)-1-butylimidazole takes place according to Example 22 by reacting 4,5-bis(4-methoxyphenyl)-2-(2-pyrrolyl)imidazole with bromobutane. Melting point 76° C.

$C_{25}H_{27}N_3O_2$ (401.5): Calculated: C 74.79 H 6.78 N 10.47. Found: C 74.51 H 7.00 N 10.28.

EXAMPLE 27

The preparation of 4,5-bis(4-methoxyphenyl)-2-(2-pyrrolyl)-1-methylimidazole is effected analogously to Example 22 by reacting 4,5bis(4-methoxyphenyl)-2-(2-pyrrolyl)imidazole with iodomethane. Melting point 134° C.

$C_{22}H_{21}N_3O_2$ (359.4): Calculated: C 73.52 H 5.89 N 11.69. Found: C 73.61 H 5.80 N 11.49.

EXAMPLE 28

0.760 g of 4,5-bis(4-methoxyphenyl)-2-(2-pyrrolyl)-1-(2-bromoethyl)imidazole is dissolved in 20 ml of dimethylformamide, combined with 0.15 g of sodium hydride (55% strength in white oil), and stirred for one hour at 60° C. The reaction mixture is poured into ice water, extracted with ethyl acetate, and separated by chromatography on silica gel, eluent ethyl acetate/hexane (2:1). Yield: 0.400 g of 2,3-bis(4-methoxyphenyl)-5,6-dihydroimidazo[1,2-a]pyrrolo[2,1-c]pyrazine, mp 172° C.

$C_{23}H_{21}N_3O_2$ (371.437): Calculated: C 74.37 H 5.71 N 11.31. Found: C 74.07 H 5.90 N 10.85.

EXAMPLE 29

1.4 g of 4,5-bis(4-methoxyphenyl)-2-(2-pyrrolyl)-1-(3-bromopropyl)imidazole is cyclized analogously to Example 28 to 0.6 g of 2,3-bis(4-methoxyphenyl)-6,7-dihydro-5H-imidazo[1,2-a]pyrrolo[2,1-c]-1,4-diazepin, mp 140° C.

EXAMPLE 30

1.53 g of 4,5-bis(4-methoxyphenyl)-2-(2-pyrrolyl)-1-(4-iodobutyl)imidazole is cyclized analogously to Example 28 to 0.85 g of 2,3-bis(4-methoxyphenyl)-5,6,7,8-tetrahydroimidazo-[1,2-a]pyrrolo[2,1-c]-1,4-diazocin, mp 181° C.

$C_{25}H_{25}N_3O_2$ (399.5): Calculated: C 75.16 H 6.31 N 10.52. Found: C 75.41 H 6.48 N 10.34.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. An imidazole derivative of the formula

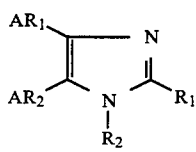

wherein
AR$_1$ and AR$_2$ each independently is phenyl, or phenyl substituted by halogen, $C_{1-4}$-alkyl, or $C_{1-4}$-alkoxy,
R$_1$ is pyrrolyl, indolyl, or imidazolyl, or one of these groups substituted by $C_{1-6}$-alkyl, carboxy, carboxy-$C_{1-4}$-alkyl, benzyl, or benzenesulfonyl, wherein any carboxy group can be esterified by a $C_{1-6}$-alkyl moiety, and wherein the point of attachment of the R$_1$ group to the imidazole ring is a C-atom; and
R$_2$ is methylene, dimethylene, trimethylene, or tetramethylene linked to the nitrogen atom of R$_1$,
or a physiologically acceptable salt thereof with an acid, or, when R$_1$ is substituted by carboxy, a physiologically acceptable salt thereof with a base.

2. An imidazole derivative of claim 1, wherein AR$_1$ and AR$_2$ each is phenyl or phenyl substituted in the para-position by fluorine, chlorine or an alkoxy group of 1-4 carbon atoms.

3. An imidazole derivative of claim 2, wherein AR$_1$ and AR$_2$ each is phenyl, 4-fluorophenyl, 4-chlorophenyl, or 4-methoxyphenyl.

4. An imidazole derivative of claim 1, wherein R$_1$ is 2-pyrrolyl, 3-pyrrolyl, 2-indolyl or, 2-imidazolyl, or one of the foregoing substituted by methyl or lower alkoxycarbonyl groups.

5. 2,3-Bis(4-methoxyphenyl)-5,6-dihydroimidazo-[1,2-a]pyrrolo[2,1-c]pyrazine, a compound of claim 1.

6. 2,3-Bis(4-methoxyphenyl)-6,7-dihydro-5H-imidazo[1,2-a]pyrrolo[2,1-c]-1,4-diazepine, a compound of claim 1.

7. 2,3-Bis(4-methoxyphenyl)-5,6,7,8-tetrahydroimidazo[1,2-a]pyrrolo[2,1-c]-1,4-diazocine, a compound of claim 1.

8. A pharmaceutical composition comprising an antiinflammtorily effective amount of a compound of claim 1 and a pharmaceutically acceptable carrier.

9. A pharmaceutical composition comprising 1-250 mg of a compound of claim 1 and 50 mg to 2 g of a pharmaceutically acceptable carrier.

10. A method of treating inflammation in a patient in need of such treatment comprising administering an amount of a compound of claim 1 effective for such treatment.

11. A method of treating an allergic disease in a patient in need of such treatment comprising administering an amount of a compound of claim 1 effective for such treatment.

12. A method of treating a migraine in a patient in need of such treatment comprising administering an amount of a compound of claim 1 effective for such treatment.

13. A method of treating dysmenorrhea in a patient in need of such treatment comprising administering an amount of a compound of claim 1 effective for such treatment.

14. A method of treating an allergic disease in a patient in need of such treatment comprising administering an effective amount of a compound of the formula

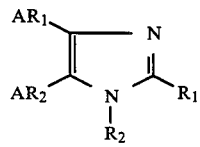

wherein
AR$_1$ and AR$_2$ each independently is phenyl, or phenyl substituted by halogen, $C_{1-4}$-alkyl, or $C_{1-4}$-alkoxy,
R$_1$ is thiazolyl or thiazolyl substituted by $C_{1-6}$-alkyl, carboxy, carboxy-$C_{1-4}$-alkyl, benzyl, or benzenesulfonyl, wherein any carboxy group can be esterified by a $C_{1-6}$-alkyl moiety, and wherein the point of attachment of the R$_1$ group to the imidazole ring is a C-atom; and
R$_2$ is hydrogen, $C_{1-6}$-alkyl, or halo-$C_{1-6}$-alkyl or is methylene, dimethylene, trimethylene, or tetramethylene linked to the nitrogen atom of R$_1$,
or a physiologically acceptable salt thereof with an acid, or, when R$_1$ is substituted by carboxy, a physiologically acceptable salt thereof with a base.

15. A method of treating a migraine in a patient in need of such treatment comprising administering an effective amount of a compound of the formula

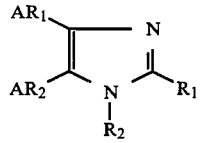

AR$_1$ and AR$_2$ each independently is phenyl, or phenyl substituted by halogen, $C_{1-4}$-alkyl, or $C_{1-4}$-alkoxy,
R$_1$ is thiazolyl or thiazolyl substituted by $C_{1-6}$-alkyl, carboxy, carboxy-$C_{1-4}$-alkyl, benzyl, or benzenesulfonyl, wherein any carboxy group can be esterified by a $C_{1-6}$-alkyl moiety, and wherein the point of attachment of the R$_1$ group to the imidazole ring is a C-atom; and $R_2$ is hydrogen, $C_{1-6}$-alkyl, or halo-$C_{1-6}$-alkyl or is methylene, dimethylene, trimethylene, or tetramethylene linked to the nitrogen atom of $R_1$, or a physiologically acceptable salt thereof with an acid, or, when $R_1$ is substituted by carboxy, a physiologically acceptable salt thereof with a base.

16. A method of treating dysmenorrhea in a patient in need of such treatment comprising administering an effective amount of a compound of the formula

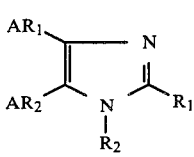

$AR_1$ and $AR_2$ each independently is phenyl, or phenyl substituted by halogen, $C_{1-4}$-alkyl, or $C_{1-4}$-alkoxy, $R_1$ is thiazolyl or thiazolyl substituted by $C_{1-6}$-alkyl, carboxy, carboxy-$C_{1-4}$-alkyl, benzyl, or benzenesulfonyl, wherein any carboxy group can be esterified by a $C_{1-6}$-alkyl moiety, and wherein the point of attachment of the $R_1$ group to the imidazole ring is a C-atom; and $R_2$ is hydrogen, $C_{1-6}$-alkyl, or halo-$C_{1-6}$-alkyl or is methylene, dimethylene, trimethylene, or tetramethylene linked to the nitrogen atom of $R_1$, or a physiologically acceptable salt thereof with an acid, or, when $R_1$ is substituted by carboxy, a physiologically acceptable salt thereof with a base.

* * * * *